United States Patent [19]

Ronning et al.

[11] Patent Number: 4,557,751

[45] Date of Patent: Dec. 10, 1985

[54] COMPOSITIONS CONTAINING SURFACTANT AND BROADLEAF FOLIAR HERBICIDE

[75] Inventors: Patricia M. Ronning; Gregg A. Vandesteeg, both of St. Paul, Minn.

[73] Assignee: Minnesota Mining and Manufacturing Company, St. Paul, Minn.

[21] Appl. No.: 242,174

[22] Filed: Mar. 10, 1981

[51] Int. Cl.$^4$ ............................................. A01N 25/30
[52] U.S. Cl. .................... 71/91; 71/DIG. 1; 71/93; 71/108; 71/116; 71/117; 71/120; 71/103
[58] Field of Search ............... 71/DIG. 1, 93, 120, 71/91, 108, 116, 117

[56] References Cited

U.S. PATENT DOCUMENTS

| Re. 30,216 | 2/1980 | Kish | 71/78 |
|---|---|---|---|
| 3,100,174 | 8/1963 | Stevens | 424/357 |
| 3,172,816 | 3/1966 | Swintosky | 167/82 |
| 3,326,664 | 6/1967 | Tso | 71/2.6 |
| 3,340,040 | 9/1967 | Tso | 71/78 |
| 3,438,765 | 4/1969 | Tso et al. | 71/78 |
| 3,620,712 | 11/1971 | Conklin | 71/106 |
| 3,954,439 | 5/1976 | Papamichael et al. | 71/93 |
| 3,990,884 | 11/1976 | Barker | 71/111 |
| 4,084,956 | 4/1978 | Doyle, Jr. et al. | 71/111 |
| 4,134,754 | 1/1979 | Hoffmann | 71/111 |
| 4,182,621 | 1/1980 | Ogata et al. | 71/76 |

OTHER PUBLICATIONS

Thompson, Agricultural Chemicals-Book II-Herbicides (1964) pp. 92 and 93.
Merck Index 9th Edition (1976) p. 584, Entry No. 4345 and p. 127, Entry No. 962.
Gulf Oil Chemical Co., Label for Carbyne.
3M Quick Reference Fact Sheet-Vistar.
Tso et al., "Inhibition of Tobacco Axillary Bud Growth with Fatty Acid Methyl Esters", *J. Agr. Food Chem.*, 13, 78 (1965).

Primary Examiner—Catherine L. Mills
Attorney, Agent, or Firm—Donald M. Sell; James A. Smith; David R. Cleveland

[57] ABSTRACT

Herbicidal compositions containing broadleaf foliar herbicide and condensate of about 2 to 40 moles of ethylene oxide with one mole of a $C_{12-18}$ unsaturated fatty acid, $C_{12-18}$ unsaturated fatty amine, $C_{12-18}$ unsaturated fatty amide, or $C_{12-18}$ unsaturated fatty alcohol.

13 Claims, No Drawings

COMPOSITIONS CONTAINING SURFACTANT AND BROADLEAF FOLIAR HERBICIDE

TECHNICAL FIELD

This invention relates to broadleaf foliar herbicide formulations. In addition, this invention relates to a method for killing broadleaf weeds.

BACKGROUND ART

Surfactants have long been used to enhance the efficacy of contact and systemic herbicides. Surfactants may provide enhanced penetration, wetting, or sticking characteristics in formulations containing surfactant and herbicide, or assist in dissolving herbicides in carriers such as water or oil. Some surfactants are often themselves herbicidal agents which act by contact or systemic action. In general, the mechanism of action of formulations containing surfactants in plants, and the manner of optimizing the choice of surfactant for use with a particular plant species, weed species, and herbicide, is not well understood.

A variety of surface-active agents (i.e., surfactants) derived from fatty acids, fatty alcohols, and esters and polyethoxylated condensate products thereof have been used as adjuvants in herbicidal or plant growth regulator formulations. For example, $C_{5-22}$ aliphatic carboxylic acids have been used to increase the solubility of a proton acceptor amino medicament or herbicide in oil in U.S. Pat. No. 3,172,816. Polyunsaturated linoleic or linolenic acids are combined with the grass herbicide "Barban" to combat wild oats in U.S. Pat. No. 4,134,754. Also, $C_{6-18}$ saturated fatty alcohols are combined with isopropyl-N-(3-chlorophenyl) carbamate to provide a composition for inhibiting tobacco sucker development in U.S. Pat. No. 3,438,765. U.S. Pat. No. Re. 30216 describes a mixture of $C_{6-18}$ saturated fatty alcohols and maleic hydrazide derivatives for tobacco sucker control, the resulting compositions also optionally containing reaction products of ethylene oxide with saturated long chain fatty acids as surface-active agents. Methyl esters of $C_{6-12}$ saturated fatty acids are mixed with fatty acid esters of polyethoxylated sorbitan (wherein the fatty acid contains about 10 to about 18 carbon atoms and wherein there are about 5 to about 80 ethoxy moieties per molecule) to provide chemical pinching agents in U.S. Pat. No. 3,620,712. Lower alkyl esters of saturated and unsaturated $C_{6-18}$ fatty acids are mixed with isopropyl-N-(3-chlorophenyl) carbamate to provide tobacco desuckering compositions in U.S. Pat. Nos. 3,326,664 and 3,340,040, and are used alone and in combination with isopropyl-N-(3-chlorophenyl) carbamate as tobacco desuckering compositions in Tso et al, "Inhibition of Tobacco Axillary Bud Growth with Fatty Acid Methyl Esters", *J. Agr. Food Chem.*, 13, 78 (1965). Condensates of ethylene oxides and various alcohols have been used in herbicide formulations, for example, in U.S. Pat. Nos. 3,990,884 (lauryl alcohol), 3,954,439 (nonyl phenol), and 4,084,956 (various saturated fatty alcohols, and oleyl alcohol, in combination with the grass herbicide "Barban").

Various surface active agents containing condensates of ethylene oxide and unsaturated fatty acids have been used in non-agricultural applications, for example, as anti-caking agents in cosmetics. Also, polyethoxylated $C_{12-26}$ saturated and unsaturated fatty acid esters have been reported for use as anti-caking and wetting agents in pesticidal formulations containing the non-herbicidally active compound 2-heptadecyl-2-imidazoline, in U.S. Pat. No. 3,100,174.

Despite all of the above reported combinations of herbicides or plant growth regulators with saturated or unsaturated fatty acids, fatty alcohols, and esters and ethylene oxide condensates thereof, and the above-described combination of the pesticide 2-heptadecyl-2-imidazoline with polyethoxylated unsaturated fatty acid esters, no broadleaf foliar herbicide formulations containing condensates of ethylene oxide and unsaturated fatty acids have been previously reported. Also, no broadleaf foliar herbicidal formulations containing condensates of ethylene oxide and unsaturated fatty amines, unsaturated fatty amides, or unsaturated fatty alcohols have been reported.

DISCLOSURE OF INVENTION

The present invention provides, in one aspect, herbicidal compositions, comprising (a) a broadleaf foliar herbicide, and (b) a surface-active agent, comprising at least one ethoxylated $C_{12-18}$ unsaturated fatty acid, ethoxylated $C_{12-18}$ unsaturated fatty amine, ethoxylated $C_{12-18}$ unsaturated fatty amide, or ethoxylated $C_{12-18}$ unsaturated fatty alcohol, said surface-active agent containing an average of about 2 to 40 oxyethylene radicals per molecule, and preferably an average of about 5 to 10 oxyethylene radicals per molecule. In addition, the present invention provides a method for controlling broadleaf weed species, comprising the step of applying to said weeds a mixture comprising a suitable diluent, a broadleaf foliar herbicide and about 0.01 to 5 percent by volume of at least one condensate of about 2 to 40 moles ethylene oxide with one mole of a $C_{12-18}$ unsaturated fatty acid, $C_{12-18}$ unsaturated fatty amine, $C_{12-18}$ unsaturated fatty amide, or $C_{12-18}$ unsaturated fatty alcohol.

DETAILED DESCRIPTION

In the practice of the present invention, the broadleaf foliar herbicides which are used include classes of herbicidal compounds such as triazines, substituted ureas, phenoxy acids, sulfonanilides, and the like. Representative compounds include 5-acetamido-2,4-dimethyltrifluoromethanesulfonanilide (commonly known as "mefluidide"), 2-chloro-4-ethylamino-6-isopropyl-S-triazine (commercially available as "AAtrex"), 3-isopropyl-1H-2-1,3-benzothiadiaza-4(3H)-one 2,2-dioxide (commercially available as "Basagran"), sodium 5-(2-chloro-4-(trifluoromethylphenoxy)-2-nitrobenzoate (commercially available as "Blazer"), 3-[p-(p-chlorophenoxy)phenyl]-1,1-dimethylurea (commercially available as "Tenoran"), 2,4-dichlorophenoxyacetic acid (commonly known as "2,4-D"), and 4-(2,4-dichlorophenoxy)butyric acid (commonly known as "2,4-DB"), as well as agriculturally acceptable salts of those compounds shown above as free acids.

The surface-active agents which are used in the present invention are certain ethoxylated unsaturated fatty acids, ethoxylated unsaturated fatty amines, ethoxylated unsaturated fatty amides, or ethoxylated unsaturated fatty alcohols. Ethoxylated unsaturated fatty acids are preferred, and ethoxylated oleates are especially preferred. Suitable unsaturated fatty acids include lauroleic acid, physeteric acid, myristoleic acid, palmitoleic acid, petroselinic acid, petroselaidic acid, oleic acid, elaidic acid, vaccenic acid, ricinoleic acid, linoleic acid, linolelaidic acid, hiragonic acid, alpha or beta eleostearic acid, punicic acid, linolenic acid, elaidolinolenic acid, psuedoeleostearic acid, moroctic acid, alpha or beta parinaric acid, and mixtures thereof. Ethoxylated unsaturated fatty acids for use in this invention can also be prepared from saponified triglycerides of unsaturated fatty acids. Suitable triglycerides of unsaturated fatty acids include triolein, trielaidin, trilinolein, trilinolenin, ricinolein, and mixtures thereof, as well as the mixture of triglycerides obtained from castor oil. Suitable unsaturated fatty amines, amides, and alcohols include the corresponding amines, amides, and alcohols of the above-described unsaturated fatty acids (e.g., oleyl amine, oleyl amide, and oleyl alcohol).

The surface-active agents used in this invention are obtained by reacting each mole of $C_{12-18}$ unsaturated fatty acids, fatty amines, fatty amides, or fatty alcohols with about 2 to 40 moles of ethylene oxide, and preferably about 5 to 10 moles of ethylene oxide, using methods well known in the art.

Surface-active agents which can be used in this invention are readily commercially available and include "Emulphor VN-430", "Emulphor EL-620", "Emulphor EL-719", and "Emulphor ON-870" from GAF, Inc., "Ethofat 0/15", "Ethofat 0/20", "Ethofat C/15", "Ethofat C/25", "Ethofat 142/20", "Diglycol Oleate L", "Ethomeen 0/15", and "Ethomid 0/15" from Armak Chemical Co., "Lipal 9C", "Lipal 15C", and "Lipal 25C" from Drew Chemical Corp., "Nopalcol 1-R", "Nopalcol 2-0", and "Nopalcol 6- 0" from Nopco Chemical Co., "Neutronyx 330" from Onyx Chemical Co., "Ethosperse OA/2" from Glyco Industries, Inc., "CPH-80-N", "CPH-40-N", "CPH-47-N", "CPH-94-N", and "CPH-81-N" from C. P. Hall Co., "Renex 20", "Brij 92", "Brij 96", and "Brij 98" from ICI, Inc., and "Siponic YX-3", "Siponic YX-5", "Siponic Y-25", and "Siponic Y500-70" from Alcolac Chemical Corp.

The herbicidal compositions of this invention are ordinarily mixed with a suitable diluent, e.g., water, ketones, alcohols, volatile aromatic solvents such as toluene, oils, and other well-known agriculturally acceptable solvents or carriers. Water is a preferred diluent. However, other diluents (e.g., 2-octanol) may be desired for use with herbicides which dissolve poorly in water, with the proviso that the chosen diluent not exhibit undue phytotoxicity against non-target plant species (e.g., agricultural crops). If desired, a hydrophilic wetting agent can be incorporated into the herbicidal compositions of this invention to assist in wetting of the target weed species. For example, alkali salts of alkylaryl sulfonates can be used in water solutions of broadleaf foliar herbicides, and alkaline earth metal soaps of alkyl aryl sulfonates can be used with emulsifiable concentrates of broadleaf foliar herbicide in oil. However, good wetting action is not always necessary to obtain good penetration of the herbicide into a plant using the herbicidal formulations of this invention.

Adjuvants such as anti-caking agents, sticking agents, pigments, fillers, stabilizers, indicators, and the like can also be used if desired. Such adjuvants can be used in amounts typically used in herbicidal formulations.

Representative broadleaf weed species which can be treated with compounds of the invention include hemp sesbania, morningglory, and sicklepod. The compositions of the invention can be applied in the presence of non-target plants in accordance with herbicidal label recommendations. Such factors as weed and crop species, plant maturity, and wind, soil, weather, and water conditions are taken into consideration in determining suitable adjustment of dosage rates and/or number of applications of the compositions of the invention to provide the desired level of weed control, without waste of the formulation and without harm to non-target plant species. Because the efficacy of the compositions of the invention is strongly influenced by the above-mentioned factors and by method of application, only general dosage guidance can be given. However, a suggested dosage rate is about 0.01 percent to 5 percent by volume of final spray of surface-active agent, and the label-recommended rate or less of broadleaf foliar herbicide. Desired treatment results can generally be obtained at a dosage rate of about 0.1 percent to 1 percent by volume of final spray of surface-active agent.

The compositions of the invention are applied using methods well known in the art. Suitable methods include broadcast or row spraying, dipping, brushing, and the like.

When the compositions of the invention are compared to compositions containing the same amount of herbicide but no surface-active agents, the compositions of the invention exhibit improved leaf penetration and decreased leaf wash-off. In addition, the compositions of the invention exhibit increased translocation, i.e., symplastic acropetal and basipetal translocation, within some plant species. Such improved penetration and increased translocation can enhance the herbicidal activity of the herbicides used in compositions of this invention.

The following examples are offered to aid understanding of the present invention and are not to be construed as limiting the scope thereof.

EXAMPLES 1-13

Herbicidal formulations containing 0.065 g/liter $^{14}C$ labeled 5-acetamido-2,4-dimethyltrifluoromethane-sulfonanilide diethanolamine salt (specific activity of 91,800 disintegrations min$^{-1}$ microgram$^{-1}$), 0.5 volume percent of one of the surface-active agents shown below in Table I, and water were prepared by mixing the ingredients together. Ten microliters of each treatment was applied to the surface of individual plant leaves of six plant species using a microliter syringe, except for hemp sesbania which received five microliters due to the small size of the leaflets and the difficulty of application. Treatments were made approximately 25 days after planting. Treatments were replicated for three plants, except in the case of soybeans. For soybeans, the last most fully expanded trifoliate of a single plant was used with each leaflet receiving one replication. Four hours after application the treated leaves were vigorously washed with methanol. An aliquant portion of the resulting wash was quantitatively analyzed for $^{14}C$ using liquid scintillation counting (LSC). Quantitative analysis of the $^{14}C$ remaining in or on the treated leaf was accomplished using in toto combustion and LSC. All plants were maintained under greenhouse conditions during the four hour exposure period. Shown below in Table I are the surface-active agent used, the plant species treated, and the percent penetration of $^{14}C$ into treated parts of the plant (expressed as a percent of recovered $^{14}C$). The number of moles of ethylene oxide per mole of acid, amine, amide, or alcohol in each surface-active agent is indicated by the notation "PO-E(X)", where X is the number of moles of ethylene oxide.

TABLE I

| Example no. | Surface-Active agent | % Penetration in plant species | | | | |
|---|---|---|---|---|---|---|
| | | SB | HS | MG | SP | CB |
| 1 | POE (5) oleate[a] | 48 | 87 | 13 | 92 | 19 |
| 2 | POE (5) oleate[b] | 46 | 84 | 10 | 94 | 18 |
| 3 | POE (10) oleate[c] | 23 | 91 | 19 | 83 | 21 |
| 4 | POE (12) linolenic and oleic acid ester[d] | 14 | 88 | 6 | 35 | 15 |
| 5 | POE (20) ricinoleate[e] | 4 | 57 | 4 | 72 | 11 |
| 6 | POE (40) ricinoleate[f] | 3 | 55 | 7 | 58 | 11 |
| 7 | POE (5) coconut fatty acid ester[g] | 44 | 63 | 22 | 87 | 17 |
| 8 | POE (5) oleyl (tert) amine[h] | 43 | 81 | 13 | 67 | 31 |
| 9 | POE (5) oleyl amide[i] | 45 | 72 | 15 | 72 | 23 |
| 10 | POE (2) oleyl alcohol[j] | 15 | 56 | 8 | 81 | 15 |
| 11 | POE (10) oleyl alcohol[k] | 38 | 71 | 30 | 64 | 41 |
| 12 | POE (20) oleyl alcohol[l] | 51 | 56 | 17 | 73 | 37 |
| 13 | POE (25) oleyl alcohol[m] | 18 | 41 | 28 | 66 | 13 |

SB = soybeans
HS = hemp sesbania
MG = morningglory
SP = sicklepod
CB = cocklebur

[a]"Emulphor VN-430", commercially available from GAF, Inc.
[b]"Ethofat O/15", commercially available from Armak Chemical Co.
[c]"Ethofat O/20", commercially available from Armak Chemical Co.
[d]"Neutronyx 330", commercially available from Onyx Chemical Co.
[e]"Emulphor EL-620" commercially available from GAF, Inc.
[f]"Emulphor EL-719" commercially available from GAF, Inc.
[g]"Ethofat C/15", commercially available from Armak Chemical Co.
[h]"Ethomeen O/15", commercially available from Armak Chemical Co.
[i]"Ethomid O/15", commercially available from Armak Chemical Co.
[j]"Ethosperse OA/2", commercially available from Glyco Industries, Inc.
[k]"Brij 96", commercially available from ICI, Inc.
[l]"Emulphor ON-870" commercially available from GAF, Inc.
[m]"Siponic Y500-70" commercially available from Alcolac Chemical Corp.

COMPARISON EXAMPLES 1-9

Using the method of Example One, several herbicidal formulations which contained a surface-active agent outside the scope of this invention were prepared and evaluated. The results are set forth below in Table II.

TABLE II

| Example No. | Surface-Active Agent | % Penetration in plant species | | | | |
|---|---|---|---|---|---|---|
| | | SB | HS | MG | SP | CB |
| 1 | Dodecyl ether of polyethylene glycol[a] | 1 | 27 | — | 10 | — |
| 2 | POE (3) $C_{12-15}$ linear primary alcohol[b] | 18 | 19 | 41 | 40 | 23 |
| 3 | POE (5) $C_{12-15}$ linear primary alcohol[c] | 20 | 23 | 46 | 42 | 21 |
| 4 | POE (7) $C_{12-15}$ linear primary alcohol[d] | 18 | 30 | 10 | 32 | 28 |
| 5 | POE (9) $C_{12-15}$ linear primary alcohol[e] | 19 | 37 | 12 | 54 | 28 |
| 6 | POE (12) $C_{12-15}$ linear primary alcohol[f] | 18 | 45 | 9 | 48 | 27 |
| 7 | POE (5) Stearate[g] | 12 | 16 | 7 | 67 | 12 |
| 8 | POE (9) stearate[h] | 21 | 45 | 3 | 55 | 13 |
| 9 | POE (10) stearate[i] | 12 | 3 | 11 | 49 | 12 |

[a]"Surfactant WK", commercially available from E. I. duPont deNemours and Co.
[b]"Tergitol 25-L-3", commercially available from Union Carbide Co.
[c]"Tergitol 25-L-5", commercially available from Union Carbide Co.
[d]"Tergitol 25-L-7", commercially available from Union Carbide Co.
[e]"Tergitol 25-L-9", commercially available from Union Carbide Co.
[f]"Tergitol 25-L-12", commercially available from Union Carbide Co.
[g]"Ethofat 60/15" commercially available from Armak Chemical Co.
[h]"Emulphor VT-650" commercially available from GAF, Inc.
[i]"Myrj 52" commercially available from ICI, Inc.

The examples and comparative examples shown above illustrate that the surface-active agents of this invention enhance the penetration of a broadleaf foliar herbicide into weed species compared to non-ionic surface-active agents of the prior art having similar chemical structure. For example, formulations containing unsaturated fatty acid esters had significantly higher penetration in hemp sesbania and sicklepod than formulations containing corresponding saturated fatty acid esters (compare, for example, Examples 1 and 3 to Comparative Example 7, and Example 3 to Comparative Example 9).

EXAMPLES 14-35

Several herbicidal formulations containing 2 volume percent POE (5) oleate ("Emulphor VN-430") and one of several broadleaf foliar herbicides in water were applied to plants ranging from 75 to 200 mm tall at time of treatment. The formulations were applied at a coverage rate of 46 liters/hectare using a "Devilbiss" brand sprayer. The amount of herbicide in the applied spray was one of two trial levels, namely the label-recommended application rate or 10% of the label-recommended application rate. Three trays of plants were treated with each formulation. Each tray contained a minimum of 6 soybean plants, 20 hemp sesbania plants, 6 morningglory plants, 20 sicklepod plants, and 6 corn plants. The treated trays of plants were randomly scattered throughout a greenhouse, and evaluated at 1, 3, 7 and 14 days after herbicide application according to the following subjective criteria:

1: No injury
2-3: minor leaf spotting or leaf burn
4-6: moderate burn or defoliation
7-9: severe burn, stunting or defoliation
10: plant death.

The results of the evaluation are shown below in Table III.

TABLE III

| Example No. | POE (5) oleate present | Herbicide | Herbicide application rate, kg/hectare | Effect on plant species | | | | |
|---|---|---|---|---|---|---|---|---|
| | | | | SB | HS | MG | SP | C |
| 14 | no | none | — | 1.7 | 1.7 | 1.7 | 1.7 | 1.0 |
| 15 | yes | none | — | 1.7 | 1.7 | 3.0 | 2.0 | 1.0 |
| 16 | no | "AAtrex" | 0.64 | 10 | 10 | 8.3 | 3.7 | 1.0 |
| 17 | yes | "AAtrex" | 0.64 | 10 | 10 | 9.3 | 9.3 | 1.3 |
| 18 | no | "AAtrex" | 0.064 | 7.7 | 9 | 5.7 | 2.3 | 1.0 |
| 19 | yes | "AAtrex" | 0.064 | 10 | 10 | 9.0 | 9.0 | 1.0 |
| 20 | no | "Tenoran" | 0.37 | 4.0 | 9.0 | 8.0 | 6.7 | 1.0 |
| 21 | yes | "Tenoran" | 0.37 | 9.0 | 10 | 10 | 10 | 3.7 |
| 22 | no | "Tenoran" | 0.037 | 1.7 | 2.7 | 2.3 | 2.0 | 1.0 |
| 23 | yes | "Tenoran" | 0.037 | 8.0 | 10 | 8.7 | 9.3 | 2.3 |
| 24 | no | "Basagran" | 0.18 | 1.7 | 1.0 | 1.7 | 1.0 | 1.0 |

TABLE III-continued

| Example No. | POE (5) oleate present | Herbicide | Herbicide application rate, kg/hectare | Effect on plant species | | | | |
|---|---|---|---|---|---|---|---|---|
| | | | | SB | HS | MG | SP | C |
| 25 | yes | "Basagran" | 0.18 | 7.7 | 8.0 | 5.7 | 8.3 | 1.7 |
| 26 | no | "Basagran" | 0.018 | 1.0 | 1.0 | 1.0 | 1.0 | 1.0 |
| 27 | yes | "Basagran" | 0.018 | 2.3 | 2.3 | 1.7 | 2.0 | 1.0 |
| 28 | no | "Blazer" | 0.092 | 2.7 | 5.0 | 5.0 | 4.0 | 1.7 |
| 29 | yes | "Blazer" | 0.092 | 8.0 | 8.3 | 8.3 | 8.0 | 8.0 |
| 30 | no | "Blazer" | 0.0092 | 1.7 | 4.0 | 2.3 | 2.7 | 1.7 |
| 31 | yes | "Blazer" | 0.0092 | 7.7 | 7.7 | 8.7 | 6.3 | 7.3 |
| 32 | no | 2,4-DB | 0.055 | 6.0 | 9.7 | 9.3 | 8.0 | 4.3 |
| 33 | yes | 2,4-DB | 0.055 | 10 | 10 | 9.0 | 10 | 4.0 |
| 34 | no | 2,4-DB | 0.0055 | 4.5 | 6.5 | 4.0 | 5.0 | 4.0 |
| 35 | yes | 2,4-DB | 0.0055 | 6.5 | 10 | 9.0 | 10 | 4.0 |

SB = soybeans
HS = hemp sesbania
MG = morningglory
SP = sicklepod
C = corn

These examples show, for example, that POE (5) oleate could be added to "AAtrex" to enable the use of "AAtrex" at reduced application rates for the removal of morningglory and sicklepod in corn without injury to corn. Without the use of POE (5) oleate, application of "AAtrex" at one-tenth the current label-recommended rate failed to control morningglory or sicklepod in corn. Also, POE (5) oleate could be added to "Tenoran" or "Basagran" to increase the effectiveness of these herbicides at low application rates against hemp sesbania, morningglory, and sicklepod in corn. In addition, POE (5) oleate improved the effectiveness of "Blazer" against hemp sesbania, morningglory, and sicklepod, and improved the effectiveness of 2,4-DB at low application rates against hemp sesbania, morningglory, and sicklepod.

EXAMPLE 36

A herbicidal formulation was prepared containing 100 microliters of a 15:15:70 (percent by volume) mixture of POE (5) oleate ("Emulphor VN 430"), POE (40) ricinoleate ("Emulphor EL 719"), and 2-octanol, together with 108.9 micrograms of $^{14}C$ labeled 5-acetamido-2,4-dimethyltrifluoromethanesulfonanilide (specific activity 91,800 disintegrations $min^{-1}$ $microgram^{-1}$) and 2,000 microliters of water. Ten microliters of the above described solution containing (0.51 g herbicide and 1.4% by volume surface-active agents) was applied to the dorsal side of the center leaflet of the second trifoliate of two 33 day old soybean plants. In control runs, three 33 day old soybean plants were treated with a similar solution containing the same radiolabeled herbicide and 5 volume percent "Citowett Plus" (commercially available from BASF-Wyandotte, Inc.), and three 33 day old soybean plants were treated with a similar solution containing the same radiolabeled herbicide but no surface-active agent at all. Four hours after application, the treated leaves were washed with two percent $NaHCO_3$ solution, water and methanol. Aliquant portions of each washing solution were quantitatively analyzed by liquid scintillation counting for $^{14}C$. Each of the plants was sectioned. The amount of $^{14}C$ present in the sectioned plants was determined using a "Tri-carb Sample Oxidizer", commercially available from Hewlett Packard. The plants which had been treated with the POE (5) oleate formulation incorporated 90.2% of the $^{14}C$ labeled herbicide, while the two groups of control plants incorporated only 26% ("Citowett Plus" treated) and 1.0% (no surface-active agent in treatment) of the $^{14}C$ labeled herbicide after four hours.

| | % Of recovered $^{14}C$ | | |
|---|---|---|---|
| Site | POE (5) oleate + POE (40) ricinoleate | "Citowett Plus" | No surface-active agent |
| Treated leaflet | 87.2 | 24.6 | 0.3 |
| Remaining leaflets of treated trifoliate | 0.6 | 0.3 | 0.0 |
| Petiole, treated trifoliate | 0.5 | 0.4 | 0.0 |
| Meristem | 0.3 | 0.1 | 0.1 |
| Upper stem | 1.1 | 0.3 | 0.6 |
| 1st trifoliate | 0.1 | 0.1 | 0.0 |
| Lower stem | 0.4 | 0.2 | 0.0 |
| Wash off | 9.8 | 74.0 | 99.0 |

This example shows that this invention provides enhanced translocation of broadleaf herbicidal compounds in plants such as soybeans.

Various modifications and alterations of this invention will be apparent to those skilled in the art without departing from the scope and spirit of this invention and the latter should not be restricted to that set forth herein for illustrative purposes.

What is claimed is:

1. Herbicidal compositions, comprising:
   (a) a broadleaf foliar herbicide, and
   (b) a surface-active agent, comprising at least one ethoxylated $C_{12-18}$ unsaturated fatty acid, ethoxylated $C_{12-18}$ unsaturated fatty amine, or ethoxylated $C_{12-18}$ unsaturated fatty amide, said surface-active agent containing an average of about 2 to 40 oxyethylene radicals per molecule.

2. Herbicidal compositions according to claim 1, wherein said surface-active agent contains an average of about 5 to 10 oxyethylene radicals per molecule.

3. Herbicidal compositions according to claim 1, further comprising a diluent, and wherein said surface-active agent is about 0.01 to 5 percent by volume of said composition.

4. Herbicidal compositions according to claim 1, wherein said broadleaf foliar herbicide is 5-acetamido-2,4-dimethyltrifluoromethanesulfonanilide, 2-chloro-4-ethylamino-6-isopropyl-S-triazine, 3-isopropyl-1H-2-1,3-benzothiadiaza-4(3H)-one 2,2-dioxide, sodium 5-(2-chloro-4-(trifluoromethylphenoxy)-2-nitrobenzoate, 3-(p-(p-chlorophenoxy)phenyl)-1, 1-dimethylurea, 2,4- dichlorophenoxyacetic acid, 4-(2,4-dichlorophenoxy)-butyric acid, or an agriculturally acceptable salt thereof.

5. Herbicidal compositions according to claim 1, wherein said surface-active agent is an ethoxylated $C_{12-18}$ unsaturated fatty acid.

6. Herbicidal compositions according to claim 5, wherein said surface-active agent is an oleate.

7. Herbicidal compositions according to claim 6, wherein said surface-active agent contains an average of about 5 to 10 oxyethylene radicals per molecule.

8. Herbicidal compositions according to claim 1, wherein said surface-active agent is an ethoxylated $C_{12-18}$ unsaturated fatty amine.

9. Herbicidal compositions according to claim 1, wherein said surface-active agent is an ethoxylated $C_{12-18}$ unsaturated fatty amide.

10. A method for controlling broadleaf weed species, comprising the step of applying to said weeds a mixture comprising a suitable diluent, a broadleaf foliar herbicide, and about 0.01 to 5 percent by volume of at least one condensate of about 2 to 40 moles ethylene oxide with one mole of a $C_{12-18}$ unsaturated fatty acid, $C_{12-18}$ unsaturated fatty amine, or $C_{12-18}$ unsaturated fatty amide.

11. A method according to claim 10, wherein said mixture contains about 0.1 to 2 percent by volume of said condensate.

12. A method according to claim 11, wherein said mixture contains at least one condensate of about 5 to 10 moles of ethylene oxide with oleic acid.

13. A method according to claim 12, wherein said broadleaf foliar herbicide is 5-acetamido-2,4-dimethyl-trifluoromethanesulfonanilide, 2-chloro-4-ethylamino-6-isopropyl-S-triazine, 3-isopropyl-1H-2-1,3-benzothiadiaza-4(3H)-one 2,2-dioxide, sodium 5-(2-chloro-4-(trifluoromethylphenoxy)-2-nitrobenzoate, 3-(p-(p-chlorophenoxy)phenyl)-1, 1-dimethylurea, 2,4-dichlorophenoxyacetic acid, 4-(2,4-dichlorophenoxy)-butyric acid, or an agriculturally acceptable salt thereof.

* * * * *